United States Patent
Valencia et al.

(10) Patent No.: US 11,306,267 B2
(45) Date of Patent: Apr. 19, 2022

(54) HYBRID TRAY FOR INTRODUCING A LOW CO2 FEED STREAM INTO A DISTILLATION TOWER

(71) Applicants: Jaime A. Valencia, Houston, TX (US); Charles J. Mart, The Woodlands, TX (US); Ransdall K. Smith, Spring, TX (US); David W. Maher, Spring, TX (US)

(72) Inventors: Jaime A. Valencia, Houston, TX (US); Charles J. Mart, The Woodlands, TX (US); Ransdall K. Smith, Spring, TX (US); David W. Maher, Spring, TX (US)

(73) Assignee: EXXONMOBIL UPSTREAM RESEARCH COMPANY, Spring, TX (US)

( * ) Notice: Subject to any disclaimer, the term of this patent is extended or adjusted under 35 U.S.C. 154(b) by 301 days.

(21) Appl. No.: 16/440,021

(22) Filed: Jun. 13, 2019

(65) Prior Publication Data
US 2020/0002634 A1 Jan. 2, 2020

Related U.S. Application Data

(60) Provisional application No. 62/691,676, filed on Jun. 29, 2018.

(51) Int. Cl.
*F25J 3/00* (2006.01)
*B01D 1/00* (2006.01)
(Continued)

(52) U.S. Cl.
CPC .............. *C10L 3/102* (2013.01); *B01D 3/008* (2013.01); *C07C 7/05* (2013.01); *F25J 1/0022* (2013.01);
(Continued)

(58) Field of Classification Search
CPC .. F25J 3/00; F25J 3/0209; F25J 3/0214; F25J 3/067; F25J 2200/04; F25J 2200/06;
(Continued)

(56) References Cited

U.S. PATENT DOCUMENTS 2,621,216 A 12/1952 White
2,843,219 A 7/1958 Habgood
(Continued)

FOREIGN PATENT DOCUMENTS

DE 3 149847 7/1983
EP 0 133 208 2/1985
(Continued)

OTHER PUBLICATIONS

Aaron, D. et al. (2005) "Separation of $CO_2$ from Flue Gas: A Review," *Separation Science and Technology*, 40, pp. 321-348.
(Continued)

*Primary Examiner* — Jianying C Atkisson
*Assistant Examiner* — Erik Mendoza-Wilkenfel
(74) *Attorney, Agent, or Firm* — Vorys, Sater, Seymour and Pease LLP

(57) ABSTRACT

A method of separating a feed stream in a distillation tower. Vapor is permitted to rise upwardly from a distillation section of the distillation tower. A feed stream is introduced into a controlled freeze zone section of the distillation tower, the controlled freeze zone section being situated above the distillation section. The feed stream is released above a level of a liquid retained by a melt tray assembly in the controlled freeze zone section. Vapor from the distillation section is directed into the liquid retained by the melt tray assembly. A solid is formed from the feed stream in the controlled freeze zone section.

8 Claims, 6 Drawing Sheets

(51) Int. Cl.
*C10L 3/10* (2006.01)
*B01D 3/00* (2006.01)
*C07C 7/05* (2006.01)
*F25J 1/00* (2006.01)
*F25J 3/02* (2006.01)

(52) U.S. Cl.
CPC ......... *F25J 3/0223* (2013.01); *C10L 2290/18* (2013.01); *C10L 2290/543* (2013.01); *F25J 2200/90* (2013.01); *F25J 2205/04* (2013.01)

(58) Field of Classification Search
CPC .. F25J 2200/08; F25J 2200/40; F25J 2200/90; F25J 2200/92; F25J 3/04903; F25J 3/04927; C10L 3/101; B01D 3/14; B01D 3/141; B01D 3/16; B01D 3/20; B01D 3/205; B01D 3/008; B01D 3/324; B01D 3/4294

See application file for complete search history.

(56) References Cited

U.S. PATENT DOCUMENTS

| | | | |
|---|---|---|---|
| 2,863,527 A | 12/1958 | Herbert | |
| 2,960,837 A | 11/1960 | Swenson et al. | |
| 3,050,950 A | 8/1962 | Karwat et al. | |
| 3,109,726 A | 11/1963 | Karwat | |
| 3,349,571 A | 10/1967 | Nebgen | |
| 3,393,527 A | 7/1968 | Swensen et al. | |
| 3,400,512 A | 9/1968 | McKay | |
| 3,419,251 A * | 12/1968 | Eckert | B05B 1/3006 261/40 |
| 3,421,984 A | 1/1969 | Jensen et al. | |
| 3,683,634 A | 8/1972 | Streich | |
| 3,705,625 A | 12/1972 | Whitten et al. | |
| 3,767,766 A | 10/1973 | Tjoa et al. | |
| 3,824,080 A | 7/1974 | Smith et al. | |
| 3,842,615 A | 10/1974 | Reigel et al. | |
| 3,848,427 A | 11/1974 | Loofbourow | |
| 3,895,101 A | 7/1975 | Tsuruta | |
| 3,929,635 A | 12/1975 | Buriks et al. | |
| 3,933,001 A | 1/1976 | Muska | |
| 4,129,626 A | 12/1978 | Mellbom | |
| 4,246,015 A | 1/1981 | Styring | |
| 4,270,937 A | 6/1981 | Adler | |
| 4,280,559 A | 7/1981 | Best | |
| 4,281,518 A | 8/1981 | Muller et al. | |
| 4,318,723 A | 3/1982 | Holmes et al. | |
| 4,319,964 A | 3/1982 | Katz et al. | |
| 4,336,233 A | 6/1982 | Appl et al. | |
| 4,344,485 A | 8/1982 | Butler | |
| 4,370,156 A | 1/1983 | Goddin et al. | |
| 4,382,912 A | 5/1983 | Madgavkar et al. | |
| 4,383,841 A | 5/1983 | Ryan et al. | |
| 4,405,585 A | 9/1983 | Sartori et al. | |
| 4,417,449 A | 11/1983 | Hegarty et al. | |
| 4,417,909 A | 11/1983 | Weltmer | |
| 4,421,535 A | 12/1983 | Mehra | |
| 4,441,900 A | 4/1984 | Swallow | |
| 4,459,142 A | 7/1984 | Goddin | |
| 4,462,814 A | 7/1984 | Holmes et al. | |
| 4,466,946 A | 8/1984 | Goddin et al. | |
| 4,511,382 A | 4/1985 | Valencia et al. | |
| 4,512,782 A | 4/1985 | Bauer et al. | |
| 4,533,372 A | 8/1985 | Valencia et al. | |
| 4,551,158 A | 11/1985 | Wagner et al. | |
| 4,563,202 A | 1/1986 | Yao et al. | |
| 4,592,766 A | 6/1986 | Kumman et al. | |
| 4,602,477 A | 7/1986 | Lucadamo | |
| 4,609,388 A | 9/1986 | Adler et al. | |
| 4,636,334 A | 1/1987 | Skinner et al. | |
| 4,695,672 A | 9/1987 | Bunting | |
| 4,697,642 A | 10/1987 | Vogel | |
| 4,710,213 A | 12/1987 | Sapper et al. | |
| 4,717,408 A | 1/1988 | Hopewell | |
| 4,720,294 A | 1/1988 | Lucadamo et al. | |
| 4,747,858 A | 5/1988 | Gottier | |
| 4,761,167 A | 8/1988 | Nicholas et al. | |
| 4,762,543 A | 8/1988 | Pantermuehl et al. | |
| 4,769,054 A | 9/1988 | Steigman | |
| 4,822,393 A | 4/1989 | Markbreiter et al. | |
| 4,831,206 A | 5/1989 | Zarchy | |
| 4,923,493 A | 5/1990 | Valencia et al. | |
| 4,927,498 A | 5/1990 | Rushmere | |
| 4,935,043 A | 6/1990 | Blanc et al. | |
| 4,954,220 A | 9/1990 | Rushmere | |
| 4,972,676 A | 11/1990 | Sakai | |
| 4,976,849 A | 12/1990 | Soldati | |
| 5,011,521 A | 4/1991 | Gottier | |
| 5,062,270 A * | 11/1991 | Haut | B01D 53/1456 62/629 |
| 5,120,338 A | 6/1992 | Potts et al. | |
| 5,137,550 A | 8/1992 | Hegarty et al. | |
| 5,152,927 A | 10/1992 | Rivers | |
| 5,233,837 A | 8/1993 | Callahan | |
| 5,240,472 A | 8/1993 | Sircar | |
| 5,247,087 A | 9/1993 | Rivers | |
| 5,265,428 A | 11/1993 | Valencia et al. | |
| 5,335,504 A | 8/1994 | Durr et al. | |
| 5,345,771 A | 9/1994 | Dinsmore | |
| 5,567,396 A | 10/1996 | Perry et al. | |
| 5,620,144 A | 4/1997 | Strock et al. | |
| 5,643,460 A | 7/1997 | Marble et al. | |
| 5,700,311 A | 12/1997 | Spencer | |
| 5,720,929 A | 2/1998 | Minkkinen et al. | |
| 5,819,555 A | 10/1998 | Engdahl | |
| 5,820,837 A | 10/1998 | Marjanovich et al. | |
| 5,899,274 A | 5/1999 | Frauenfeld et al. | |
| 5,956,971 A | 9/1999 | Cole et al. | |
| 5,964,985 A | 10/1999 | Wootten | |
| 5,983,663 A | 11/1999 | Sterner | |
| 6,053,007 A | 4/2000 | Victory et al. | |
| 6,053,484 A | 4/2000 | Fan et al. | |
| 6,082,133 A | 7/2000 | Barclay et al. | |
| 6,082,373 A | 7/2000 | Sakurai et al. | |
| 6,162,262 A | 12/2000 | Minkkinen et al. | |
| 6,223,557 B1 | 5/2001 | Cole | |
| 6,240,744 B1 | 6/2001 | Agrawal et al. | |
| 6,267,358 B1 | 7/2001 | Gohara et al. | |
| 6,270,557 B1 | 8/2001 | Millet et al. | |
| 6,274,112 B1 | 8/2001 | Moffett et al. | |
| 6,336,334 B1 | 1/2002 | Minkkinen et al. | |
| 6,374,634 B2 | 4/2002 | Gallarda et al. | |
| 6,401,486 B1 | 6/2002 | Lee et al. | |
| 6,416,729 B1 | 7/2002 | DeBerry et al. | |
| 6,442,969 B1 | 9/2002 | Rojey et al. | |
| 6,500,982 B1 | 12/2002 | Hale et al. | |
| 6,505,683 B2 | 1/2003 | Minkkinen et al. | |
| 6,516,631 B1 | 2/2003 | Trebble | |
| 6,517,801 B2 | 2/2003 | Watson et al. | |
| 6,539,747 B2 | 4/2003 | Minta et al. | |
| 6,565,629 B1 | 5/2003 | Hayashida et al. | |
| 6,605,138 B2 | 8/2003 | Frondorf | |
| 6,631,626 B1 | 10/2003 | Hahn | |
| 6,632,266 B2 | 10/2003 | Thomas et al. | |
| 6,662,872 B2 | 12/2003 | Gutek et al. | |
| 6,708,759 B2 | 3/2004 | Leaute et al. | |
| 6,711,914 B2 | 3/2004 | Lecomte | |
| 6,735,979 B2 | 5/2004 | Lecomte et al. | |
| 6,755,251 B2 | 6/2004 | Thomas et al. | |
| 6,755,965 B2 | 6/2004 | Pironti et al. | |
| 6,818,194 B2 | 11/2004 | DeBerry et al. | |
| 6,883,327 B2 | 4/2005 | Iijima et al. | |
| 6,946,017 B2 | 9/2005 | Leppin et al. | |
| 6,958,111 B2 | 10/2005 | Rust et al. | |
| 6,962,061 B2 | 11/2005 | Wilding et al. | |
| 7,001,490 B2 | 2/2006 | Wostbrock et al. | |
| 7,004,985 B2 | 2/2006 | Wallace et al. | |
| 7,066,986 B2 | 6/2006 | Haben et al. | |
| 7,073,348 B2 | 7/2006 | Clodic et al. | |
| 7,121,115 B2 | 10/2006 | Lemaire et al. | |
| 7,128,150 B2 | 10/2006 | Thomas et al. | |
| 7,128,276 B2 | 10/2006 | Nilsen et al. | |
| 7,152,431 B2 | 12/2006 | Amin et al. | |

(56) References Cited

U.S. PATENT DOCUMENTS

| | | | |
|---|---|---|---|
| 7,211,128 B2 | 5/2007 | Thomas et al. | |
| 7,211,701 B2 | 5/2007 | Muller et al. | |
| 7,219,512 B1 | 5/2007 | Wilding et al. | |
| 7,285,225 B2 | 10/2007 | Copeland et al. | |
| 7,325,415 B2 | 2/2008 | Amin et al. | |
| 7,424,808 B2 | 9/2008 | Mak | |
| 7,437,889 B2 | 10/2008 | Roberts et al. | |
| 7,442,231 B2 | 10/2008 | Landrum | |
| 7,442,233 B2 | 10/2008 | Mitariten | |
| 7,493,779 B2 | 2/2009 | Amin | |
| 7,536,873 B2 | 5/2009 | Nohlen | |
| 7,550,064 B2 | 6/2009 | Bassler et al. | |
| 7,575,624 B2 | 8/2009 | Cartwright et al. | |
| 7,597,746 B2 | 10/2009 | Mak et al. | |
| 7,635,408 B2 | 12/2009 | Mak et al. | |
| 7,637,984 B2 | 12/2009 | Adamopoulos | |
| 7,637,987 B2 | 12/2009 | Mak | |
| 7,641,717 B2 | 1/2010 | Gal | |
| 7,662,215 B2 | 2/2010 | Sparling et al. | |
| 7,691,239 B2 | 4/2010 | Kister et al. | |
| 7,722,289 B2 | 5/2010 | Leone et al. | |
| 7,729,976 B2 | 6/2010 | Hill et al. | |
| 7,770,872 B2 | 8/2010 | Delatour | |
| 7,795,483 B2 | 9/2010 | Kulprathipanja et al. | |
| 7,806,965 B2 | 10/2010 | Stinson | |
| 7,814,975 B2 | 10/2010 | Hagen et al. | |
| 7,879,135 B2 | 2/2011 | Ravikumar et al. | |
| 7,901,583 B2 | 3/2011 | McColl et al. | |
| 7,955,496 B2 | 6/2011 | Iqbal et al. | |
| 8,002,498 B2 | 8/2011 | Leone et al. | |
| 8,020,408 B2 | 9/2011 | Howard et al. | |
| 8,133,764 B2 | 3/2012 | Dirks et al. | |
| 8,136,799 B2 | 3/2012 | Griepsma | |
| 8,303,685 B2 | 11/2012 | Schubert et al. | |
| 8,308,849 B2 | 11/2012 | Gal | |
| 8,312,738 B2 | 11/2012 | Singh et al. | |
| 8,372,169 B2 | 2/2013 | Tsangaris et al. | |
| 8,381,544 B2 | 2/2013 | Coyle | |
| 8,388,832 B2 | 3/2013 | Moffett et al. | |
| 8,428,835 B2 | 4/2013 | Habert et al. | |
| 8,475,572 B2 | 7/2013 | Prast et al. | |
| 8,500,105 B2 | 8/2013 | Nieuwoudt | |
| 8,529,662 B2 | 9/2013 | Kelley et al. | |
| 9,739,529 B2 | 8/2017 | Northrop et al. | |
| 10,201,765 B2 | 2/2019 | Alzner et al. | |
| 2002/0174687 A1 | 11/2002 | Cai | |
| 2002/0189443 A1 | 12/2002 | McGuire | |
| 2003/0181772 A1 | 9/2003 | Meyer et al. | |
| 2006/0207946 A1 | 9/2006 | McColl et al. | |
| 2006/0239879 A1 | 10/2006 | Lallemand et al. | |
| 2007/0056317 A1 | 3/2007 | Amin et al. | |
| 2007/0144943 A1 | 6/2007 | Lemaire et al. | |
| 2007/0277674 A1 | 12/2007 | Hirano et al. | |
| 2008/0034789 A1 | 2/2008 | Fieler et al. | |
| 2008/0091316 A1 | 4/2008 | Szczublewski | |
| 2008/0092589 A1 | 4/2008 | Trainer et al. | |
| 2008/0307827 A1 | 12/2008 | Hino et al. | |
| 2009/0023605 A1 | 1/2009 | Lebl et al. | |
| 2009/0049864 A1* | 2/2009 | Kovak | B01J 19/305 62/643 |
| 2009/0220406 A1 | 9/2009 | Rahman | |
| 2010/0011809 A1 | 1/2010 | Mak | |
| 2010/0018248 A1 | 1/2010 | Fieler et al. | |
| 2010/0024472 A1 | 2/2010 | Amin et al. | |
| 2010/0064725 A1 | 3/2010 | Chieng et al. | |
| 2010/0107687 A1 | 5/2010 | Andrian et al. | |
| 2010/0132405 A1 | 6/2010 | Nilsen | |
| 2010/0147022 A1 | 6/2010 | Hart et al. | |
| 2010/0187181 A1 | 7/2010 | Sortwell | |
| 2010/0310439 A1 | 12/2010 | Brok et al. | |
| 2011/0132034 A1 | 6/2011 | Beaumont et al. | |
| 2011/0154856 A1 | 6/2011 | Andrian et al. | |
| 2011/0168019 A1 | 7/2011 | Northrop et al. | |
| 2011/0192190 A1 | 8/2011 | Andrian et al. | |
| 2011/0265512 A1 | 11/2011 | Bearden et al. | |
| 2012/0006055 A1 | 1/2012 | Van Santen et al. | |
| 2012/0031143 A1 | 2/2012 | Van Santem et al. | |
| 2012/0031144 A1 | 2/2012 | Northrop et al. | |
| 2012/0079852 A1 | 4/2012 | Northrop et al. | |
| 2012/0103193 A1 | 5/2012 | Polderman | |
| 2012/0125043 A1 | 5/2012 | Cullinane et al. | |
| 2012/0204599 A1 | 8/2012 | Northrop et al. | |
| 2012/0279728 A1 | 11/2012 | Northrop et al. | |
| 2013/0032029 A1 | 2/2013 | Mak | |
| 2013/0074541 A1 | 3/2013 | Kaminsky et al. | |
| 2013/0098105 A1 | 4/2013 | Northrop | |
| 2014/0137599 A1 | 5/2014 | Oelfke et al. | |
| 2015/0158796 A1 | 6/2015 | Valencia et al. | |
| 2015/0159939 A1 | 6/2015 | Valencia et al. | |
| 2015/0159940 A1 | 6/2015 | Valencia et al. | |
| 2015/0159941 A1 | 6/2015 | Valencia et al. | |
| 2015/0159942 A1 | 6/2015 | Valencia et al. | |
| 2015/0159943 A1 | 6/2015 | Valencia et al. | |
| 2015/0159944 A1 | 6/2015 | Valencia et al. | |
| 2015/0159945 A1 | 6/2015 | Valencia et al. | |
| 2015/0159946 A1 | 6/2015 | Valencia et al. | |
| 2015/0159947 A1 | 6/2015 | Valencia et al. | |
| 2015/0362251 A1* | 12/2015 | Oelfke | B01D 3/32 62/637 |
| 2016/0040929 A1 | 2/2016 | Hammon et al. | |

FOREIGN PATENT DOCUMENTS

| | | |
|---|---|---|
| EP | 0 508 244 | 10/1992 |
| EP | 1 338 557 | 3/2005 |
| GB | 1010403 | 11/1965 |
| WO | WO 2002/032536 | 4/2002 |
| WO | WO 2002/039038 | 5/2002 |
| WO | WO 2004/047956 | 6/2004 |
| WO | WO 2008/034789 | 3/2008 |
| WO | WO 2008/095258 | 8/2008 |
| WO | WO 2008/152030 | 12/2008 |
| WO | WO 2009/023605 | 2/2009 |
| WO | WO 2009/029353 | 3/2009 |
| WO | WO 2009/087206 | 7/2009 |
| WO | WO 2010/023238 | 3/2010 |
| WO | WO 2010/052299 | 5/2010 |
| WO | WO 2010/136442 | 12/2010 |
| WO | WO 2011/026170 | 3/2011 |
| WO | WO 2013/095828 | 6/2013 |
| WO | WO 2013/142100 | 9/2013 |

OTHER PUBLICATIONS

Amin, R. (2003) "Advanced Mini Natural Gas Liquefier," *LNG Journal*, Mar.-Apr. 2003, pp. 20-23.

Black, S. (2006) "Chilled Ammonia Process for CO2 Capture," *Alstom Position Paper*, Nov. 2006, 6 pgs.

Ciulla, Vincent (2007) "How the Engine Works," About.com, Mar. 21, 2007, [retrieved from the internet on Aug. 17, 2012]. <URL: http://autorepair.about.com/cs/generalinfo/a/aa060500a.html>.

"Cryogenics" *Science Clarified*, May 2, 2006 [retrieved from the internet on Aug. 17, 2012]. <URL: http://www.scienceclarified.com/Co-Di/Cryogenics.html>.

Denton, R. D. et al. (1985) "Integrated Low Temperature Processing of Sour Natural Gas," *Gas Processors Assoc., 64th Ann. Conv.*, pp. 92-96.

Guccione, E. (1963) "New Approach to Recovery of Helium from Natural Gas," *Chem. Engr.*, Sep. 30, 1963, pp. 76-78.

Hassan, S. M. N. (2005) "Techno-Economic Study of CO$_2$ Capture Process for Cement Plants," *University of Waterloo—Thesis*.

Haut, R. C. et al. (1988) "Development and Application of the Controlled Freeze Zone Process," *SPE 17757, SPE Gas Tech. Symp.—Dallas, TX*, pp. 435-443.

Haut, R. C. et al. (1988) "Development and Application of the Controlled Freeze Zone Process," *OSEA 88197, 7th Offshore So. East Asia Conf., Singapore*, Feb. 1988, pp. 840-848.

Haut, R. C. et al. (1989) "Development and Application of the Controlled Freeze Zone Process," *SPE Production Engineering*, Aug. 1989, pp. 265-271.

(56) References Cited

OTHER PUBLICATIONS

Im, U. K. et al. (1971) "Heterogeneous Phase Behavior of Carbon Dioxide in *n*-Hexane and *n*-Heptane at Low Temperatures," *Jrnl. of Chem. Engineering Data*, v. 16.4, pp. 412-415.

Mitariten, M. et al. (2007) "The Sorbead™ Quick-Cycle Process for Simultaneous Removal of Water, Heavy Hydrocarbons and Mercaptans from Natural Gas," *Laurance Reid Gas Conditioning Conf.*, Feb. 25-27, 2007.

Northrop, P. Scott et al. (2004) "Cryogenic Sour Gas Process Attractive for Acid Gas Injection Applications," $83^{rd}$ *Ann. Gas Processors Assoc. Convention, New Orleans, LA.*, pp. 1-8 (XP007912217).

Pagcatipunan, C. et al. (2005) "Maximize the Performance of Spray Nozzle Systems," *CEP Magazine*, Dec. 2005, pp. 38-44.

Reyes, S. C. et al. (1997) "Frequency Modulation Methods for Diffusion and Adsorption Measurements in Porous Solids," *J. Phys. Chem. B*, v.101, pp. 614-622.

Rubin, E. S. et al. (2002) "A Technical, Economic and Environmental Assessment of Amine-based CO2 Capture Technology for Power Plant Greenhouse Gas Control," *U.S. Dept. of Energy*, Oct. 2002, DOE/DE-FC26-00NT40935, 26 pages.

Spero, C. (2007) "Callide Oxyfuel Project," *CS Energy, cLET Seminar*, Jul. 12, 2007, 9 pages.

Thomas, E. R. et al. (1987) "Conceptual Studies Using the Controlled Freeze Zone (CFZ) Process," *AIChE Summer Nat'l Mtg.*, Aug. 16-19, 1987.

Thomas, E. R. et al. (1988) "Conceptual Studies for $CO_2$/Natural Gas Separation Using the Control Freeze Zone (CFZ) Process," *Gas Separation and Purification*, v. 2, pp. 84-89.

Valencia, J. A. et al. (2008) "Controlled Freeze Zone™ Technology for Enabling Processing of High $CO_2$ and $H_2S$ Gas Reserves," SPE-IPTC 12708, Kuala Lumpur, IN, v.4.1, Jan. 2008, pp. 2358-2363.

Victory, D. J. et al. (1987) "The CFZ Process: Direct Methane-Carbon Dioxide Fractionation," $66^{th}$ *Ann. GPA Convention*, Mar 16-18, Denver, CO.

Wilson, R.W. et al. (1968) "Helium: Its Extraction and Purification," *Journ. Petrol. Tech.*, v. 20, pp. 341-344.

\* cited by examiner

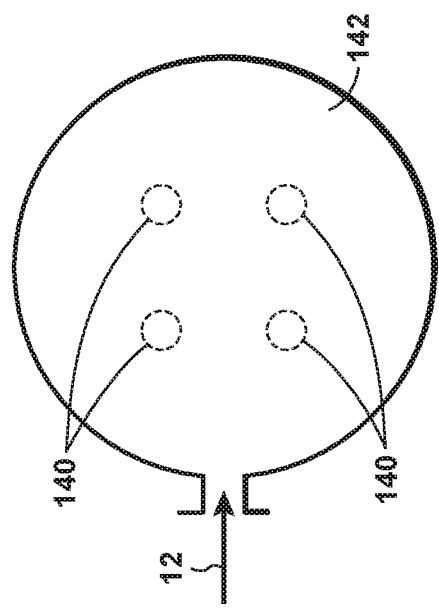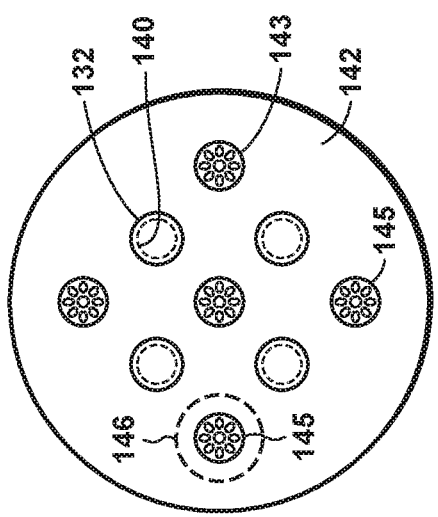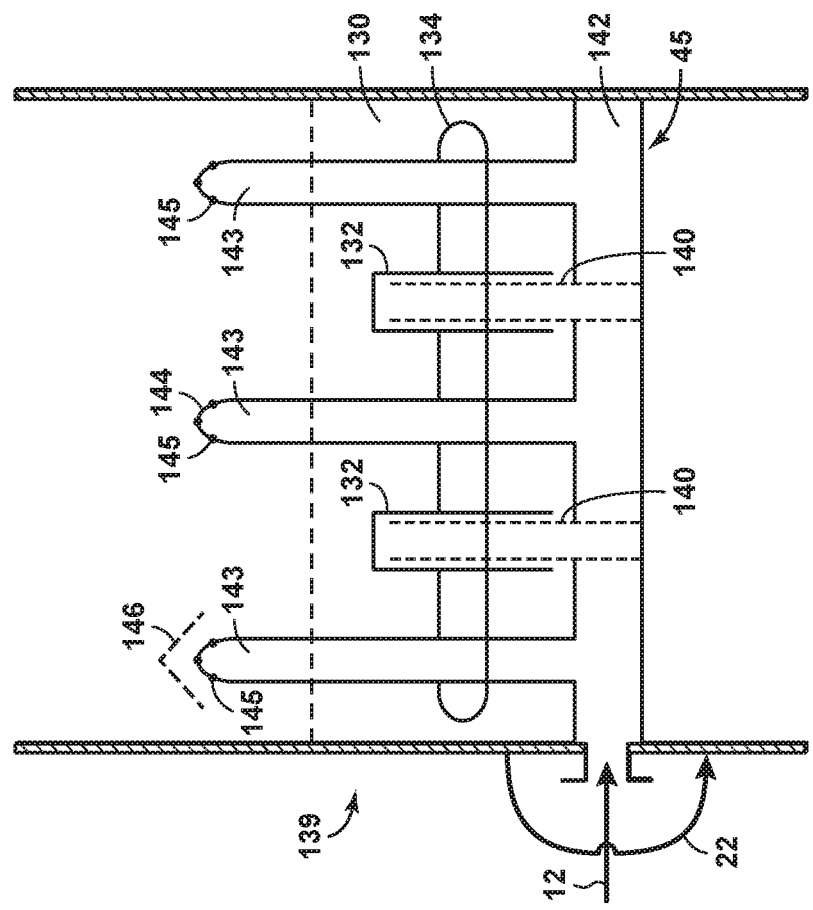

HYBRID TRAY FOR INTRODUCING A LOW CO2 FEED STREAM INTO A DISTILLATION TOWER

CROSS REFERENCE TO RELATED APPLICATIONS

This application claims the priority benefit of U.S. Provisional Patent Application No. 62/691,676 filed Jun. 29, 2018, entitled HYBRID TRAY FOR INTRODUCING A LOW CO2 FEED STREAM INTO A DISTILLATION TOWER.

This application is related to but does not claim priority to U.S. Provisional patent application Nos. 61/912,975 filed Dec. 6, 2013 and titled METHOD AND SYSTEM FOR SEPARATING A FEED STREAM WITH A FEED STREAM DISTRIBUTION MECHANISM; 61/912,957 filed on Dec. 6, 2013 and titled METHOD AND DEVICE FOR SEPARATING HYDROCARBONS AND CONTAMINANTS WITH A SPRAY ASSEMBLY; 62/044,770 filed on Sep. 2, 2014 and titled METHOD AND DEVICE FOR SEPARATING HYDROCARBONS AND CONTAMINANTS WITH A SPRAY ASSEMBLY; 61/912,959 filed on Dec. 6, 2013 and titled METHOD AND SYSTEM OF MAINTAINING A LIQUID LEVEL IN A DISTILLATION TOWER; 61/912,964 filed on Dec. 6, 2013 and titled METHOD AND DEVICE FOR SEPARATING A FEED STREAM USING RADIATION DETECTORS; 61/912,970 filed on Dec. 6, 2013 and titled METHOD AND SYSTEM OF DEHYDRATING A FEED STREAM PROCESSED IN A DISTILLATION TOWER; 61/912,978 filed on Dec. 6, 2013 and titled METHOD AND SYSTEM FOR PREVENTING ACCUMULATION OF SOLIDS IN A DISTILLATION TOWER; 61/912,983 filed on Dec. 6, 2013 and titled METHOD OF REMOVING SOLIDS BY MODIFYING A LIQUID LEVEL IN A DISTILLATION TOWER; 61/912,984 filed on Dec. 6, 2013 and titled METHOD AND SYSTEM OF MODIFYING A LIQUID LEVEL DURING START-UP OPERATIONS; 61/912,986 filed on Dec. 6, 2013 and titled METHOD AND DEVICE FOR SEPARATING HYDROCARBONS AND CONTAMINANTS WITH A HEATING MECHANISM TO DESTABILIZE AND/OR PREVENT ADHESION OF SOLIDS; 61/912,987 filed on Dec. 6, 2013 and titled METHOD AND DEVICE FOR SEPARATING HYDROCARBONS AND CONTAMINANTS WITH A SURFACE TREATMENT MECHANISM.

This application is also related to U.S. Application No. 62/691,679, titled MIXING AND HEAT INTEGRATION OF MELT TRAY LIQUIDS IN A CRYOGENIC DISTILLATION TOWER, having common inventors with this application, and filed on the same date as this application.

BACKGROUND

Fields of Disclosure

The disclosure relates generally to the field of fluid separation. More specifically, the disclosure relates to the cryogenic separation of contaminants, such as acid gas, from a hydrocarbon.

Description of Related Art

This section is intended to introduce various aspects of the art, which may be associated with the present disclosure. This discussion is intended to provide a framework to facilitate a better understanding of particular aspects of the present disclosure. Accordingly, it should be understood that this section should be read in this light, and not necessarily as admissions of prior art.

The production of natural gas hydrocarbons, such as methane and ethane, from a reservoir oftentimes carries with it the incidental production of non-hydrocarbon gases. Such gases include contaminants, such as at least one of carbon dioxide ("$CO_2$"), hydrogen sulfide ("$H_2S$"), carbonyl sulfide, carbon disulfide and various mercaptans. When a feed stream being produced from a reservoir includes these contaminants mixed with hydrocarbons, the stream is oftentimes referred to as "sour gas."

Many natural gas reservoirs have relatively low percentages of hydrocarbons and relatively high percentages of contaminants. Contaminants may act as a diluent and lower the heat content of hydrocarbons. Some contaminants, like sulfur-bearing compounds, are noxious and may even be lethal. Additionally, in the presence of water some contaminants can become quite corrosive.

It is desirable to remove contaminants from a stream containing hydrocarbons to produce sweet and concentrated hydrocarbons. Specifications for pipeline quality natural gas typically call for a maximum of 2-4% $CO_2$ and ¼ grain $H_2S$ per 100 scf (4 ppmv) or 5 mg/Nm3 $H_2S$. Specifications for lower temperature processes such as natural gas liquefaction plants or nitrogen rejection units typically require less than 50 ppm $CO_2$.

The separation of contaminants from hydrocarbons is difficult and consequently significant work has been applied to the development of hydrocarbon/contaminant separation methods. These methods can be placed into three general classes: absorption by solvents (physical, chemical and hybrids), adsorption by solids, and distillation.

Separation by distillation of some mixtures can be relatively simple and, as such, is widely used in the natural gas industry. However, distillation of mixtures of natural gas hydrocarbons, primarily methane, and one of the most common contaminants in natural gas, carbon dioxide, can present significant difficulties. Conventional distillation principles and conventional distillation equipment are predicated on the presence of only vapor and liquid phases throughout the distillation tower. The separation of $CO_2$ from methane by distillation involves temperature and pressure conditions that result in solidification of $CO_2$ if a pipeline or better quality hydrocarbon product is desired. The required temperatures are cold temperatures typically referred to as cryogenic temperatures.

Certain cryogenic distillations can overcome the above mentioned difficulties. These cryogenic distillations provide the appropriate mechanism to handle the formation and subsequent melting of solids during the separation of solid-forming contaminants from hydrocarbons. The formation of solid contaminants in equilibrium with vapor-liquid mixtures of hydrocarbons and contaminants at particular conditions of temperature and pressure takes place in a controlled freeze zone (CFZ) section. A lower section may also help separate the contaminants from the hydrocarbons but the lower section is operated at a temperature and pressure that does not form solid. Cryogenic distillation towers using controlled freeze zone technologies may effectively process very sour gas streams (i.e., between about 20% to more than 70% $CO_2$ and/or $H_2S$).

In known CFZ applications, a feed stream is dried and precooled to about −60° F. before introduction to the CFZ tower below the CFZ section and melt tray. The vapor component of the cooled feed stream combines with the vapor rising from the stripping section of the tower and bubbles through the liquid on the melt tray. This serves several beneficial purposes, including: the rising vapor stream is cooled and a portion of the $CO_2$ is condensed, resulting in a cooler and cleaner gas stream entering the open portion of the CFZ spray chamber; the rising vapor stream is evenly distributed across the tower cross section as it enters the CFZ spray chamber. Most of the required melt tray heat input is provided via sensible heat from cooling the vapor and latent heat from condensing a portion of the $CO_2$ in the gas stream; and the melt tray liquid is vigorously mixed, which facilitates melting of solid $CO_2$ particles falling into the melt tray with the bulk liquid temperature only 2 to 3 degrees F. above the melting point of $CO_2$.

A conventional CFZ unit with feed vapor entering below the melt tray can be used to process sour gas with $CO_2$ content significantly below 20%, however this has important disadvantages. Most significantly, when the lower $CO_2$ content feed vapor bubbles through the melt tray liquid, the $CO_2$ in the vapor rising into the open portion of the CFZ section will increase to the equilibrium dictated by required melt tray operating conditions. This would then require the overhead refrigeration system and associated equipment to be larger than would otherwise be required if the feed vapor were introduced immediately above the melt tray in its leaner state. Another disadvantage is the undesirable melt tray cooling that occurs due to the latent heat from vaporizing some of the $CO_2$ contained in the melt tray liquid to reach equilibrium with the feed vapor. This impact could be mitigated by decreasing the feed cooling and thereby providing additional sensible heat in the feed vapor.

It has been proposed to introduce feed stream above the melt tray, but these proposals have significant disadvantages. In one example, one or more feed stream inlet nozzles may be attached to one or more distribution headers at the desired location, within the open portion of the CFZ section. While this would introduce the gas evenly across the tower cross section, a major disadvantage of this solution is the potential for fouling of the headers and supports with solid $CO_2$.

Another method of introducing feed stream above the melt tray is shown in U.S. Patent Application Publication No. 2015/0362251, incorporated herein by reference, which uses a sleeve in the CFZ spray chamber and introduces the feed stream via an annular space between the pressure containing tower wall and the sleeve that otherwise is not required. This approach avoids distribution headers that could become fouled with solid $CO_2$. However, the feed vapor is introduced evenly around the outer edge of the tower cross section, not evenly across the full tower cross section as desired. This will result in undesirable flow patterns in the CFZ section and an uneven distribution of $CO_2$ solids falling into the melt tray liquid. The uneven distribution of solids falling into the melt tray will make it more difficult to reliably melt the solids while operating at the desired melt tray liquid temperature. Also, if the position of the sleeve does not remain concentric with the tower during operation, feed introduction to the tower will also be maldistributed around the circumference. Another disadvantage of this method is that the sleeve required for this approach adds cost and mechanical complexity vs. the standard CFZ design. What is needed is a method of using a cryogenic distillation process, such as a CFZ distillation process, that can reliably and economically process feed stream with less that 20% $CO_2$ content.

SUMMARY

The present disclosure provides a device and method for separating contaminants from hydrocarbons, among other things.

Aspects of the disclosure provide a distillation tower for separating a feed stream. The distillation tower includes a distillation section permitting vapor to rise upwardly therefrom, and a controlled freeze zone section situated above the distillation section. The controlled freeze zone is constructed and arranged to form a solid from a feed stream. The controlled freeze zone section includes a spray assembly in the controlled freeze zone upper section, and a melt tray assembly in the controlled freeze zone lower section. The melt tray assembly includes a feed stream manifold that directs the feed stream into the distillation tower. At least one vapor stream riser directs the vapor from the distillation section into liquid retained by the melt tray assembly. At least one feed stream riser having a lower end operationally connected to the feed stream manifold and an upper end positioned above a level of the liquid retained by the melt tray assembly. The feed stream is released above the level of the liquid retained by the melt tray assembly.

In another aspect, a method of separating a feed stream in a distillation tower is provided. Vapor is permitted to rise upwardly from a distillation section of the distillation tower. A feed stream is introduced into a controlled freeze zone section of the distillation tower. The controlled freeze zone section is situated above the distillation section. The feed stream is released above a level of a liquid retained by a melt tray assembly in the controlled freeze zone section. Vapor from the distillation section is directed into the liquid retained by the melt tray assembly. A solid is formed from the feed stream in the controlled freeze zone section.

The foregoing has broadly outlined the features of the present disclosure in order that the detailed description that follows may be better understood. Additional features will also be described herein.

BRIEF DESCRIPTION OF THE DRAWINGS

These and other features, aspects and advantages of the disclosure will become apparent from the following description, appending claims and the accompanying drawings, which are briefly described below.

FIG. 5 is a side view of a middle controlled freeze zone section of a distillation tower according to disclosed aspects.

FIG. 6 is a bottom view of the middle controlled feed zone of FIG. 5.

FIG. 7 is a top view of the middle controlled feed zone of FIG. 5.

Figure 1:
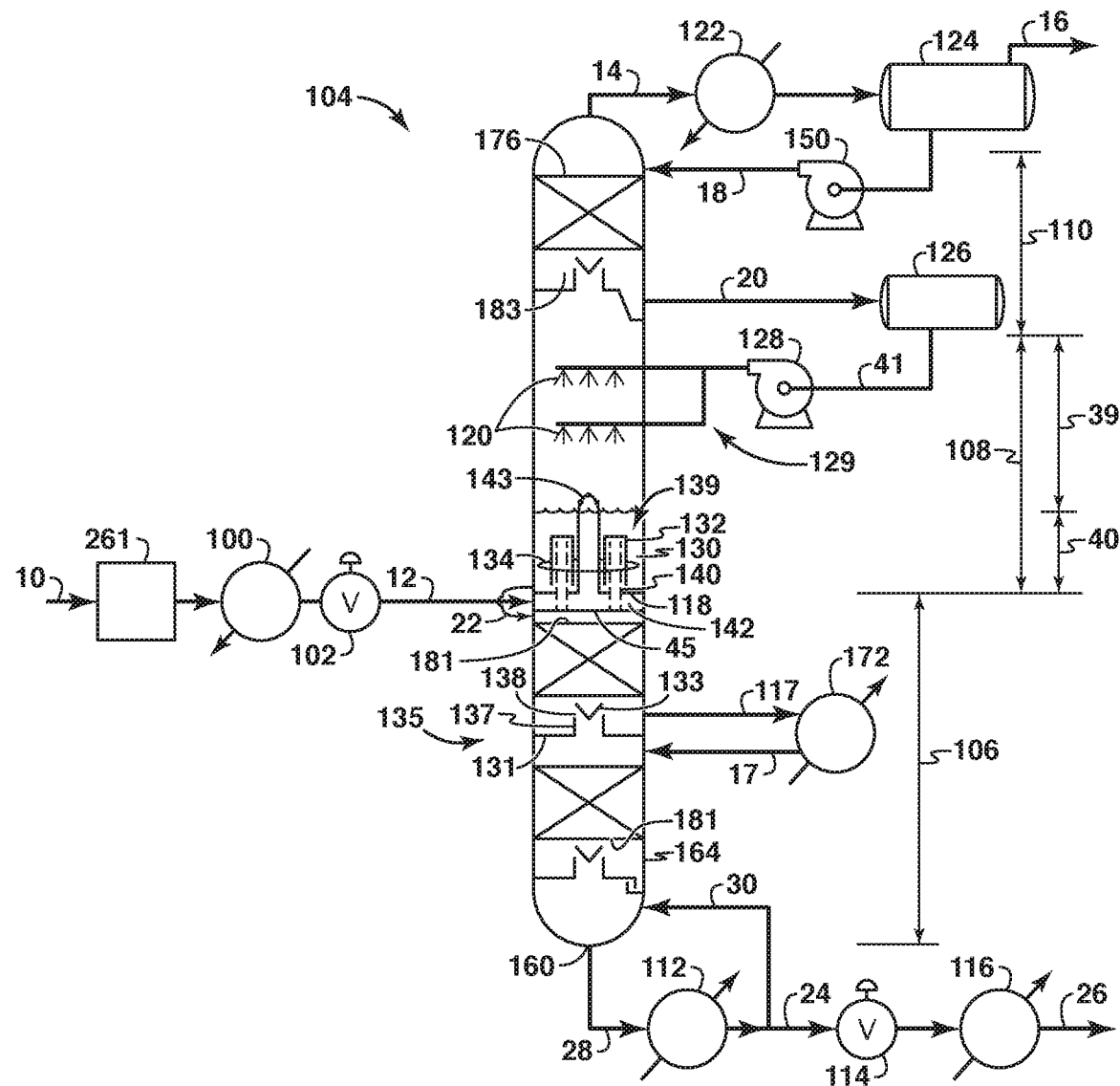
FIG. 1 is a schematic diagram of a tower with sections within a single vessel according to disclosed aspects.

It should be noted that the figures are merely examples and no limitations on the scope of the present disclosure are intended thereby. Further, the figures are generally not drawn to scale, but are drafted for purposes of convenience and clarity in illustrating various aspects of the disclosure.

DETAILED DESCRIPTION

For the purpose of promoting an understanding of the principles of the disclosure, reference will now be made to the features illustrated in the drawings and specific language will be used to describe the same. It will nevertheless be understood that no limitation of the scope of the disclosure is thereby intended. Any alterations and further modifications, and any further applications of the principles of the disclosure as described herein are contemplated as would normally occur to one skilled in the art to which the disclosure relates. It will be apparent to those skilled in the relevant art that some features that are not relevant to the present disclosure may not be shown in the drawings for the sake of clarity.

As referenced in this application, the terms "stream," "gas stream," "vapor stream," and "liquid stream" refer to different stages of a feed stream as the feed stream is processed in a distillation tower that separates methane, the primary hydrocarbon in natural gas, from contaminants. Although the phrases "gas stream," "vapor stream," and "liquid stream," refer to situations where a gas, vapor, and liquid is mainly present in the stream, respectively, there may be other phases also present within the stream. For example, a gas may also be present in a "liquid stream." In some instances, the terms "gas stream" and "vapor stream" may be used interchangeably.

The articles "the", "a" and "an" are not necessarily limited to mean only one, but rather are inclusive and open ended so as to include, optionally, multiple such elements.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numeral ranges provided. Accordingly, these terms should be interpreted as indicating that insubstantial or inconsequential modifications or alterations of the subject matter described are considered to be within the scope of the disclosure.

The disclosure relates to a system and method for separating a feed stream in a distillation tower. The system and method helps optimally match where the feed stream should enter the distillation tower based on the concentrations of components in the feed stream so as to improve energy efficiency and/or optimally size the distillation tower. The system and method may also help prevent the undesired accumulation of solids in the controlled freeze zone section of the distillation tower. FIGS. 1-8 of the disclosure display various aspects of the system and method.

Figure 2:
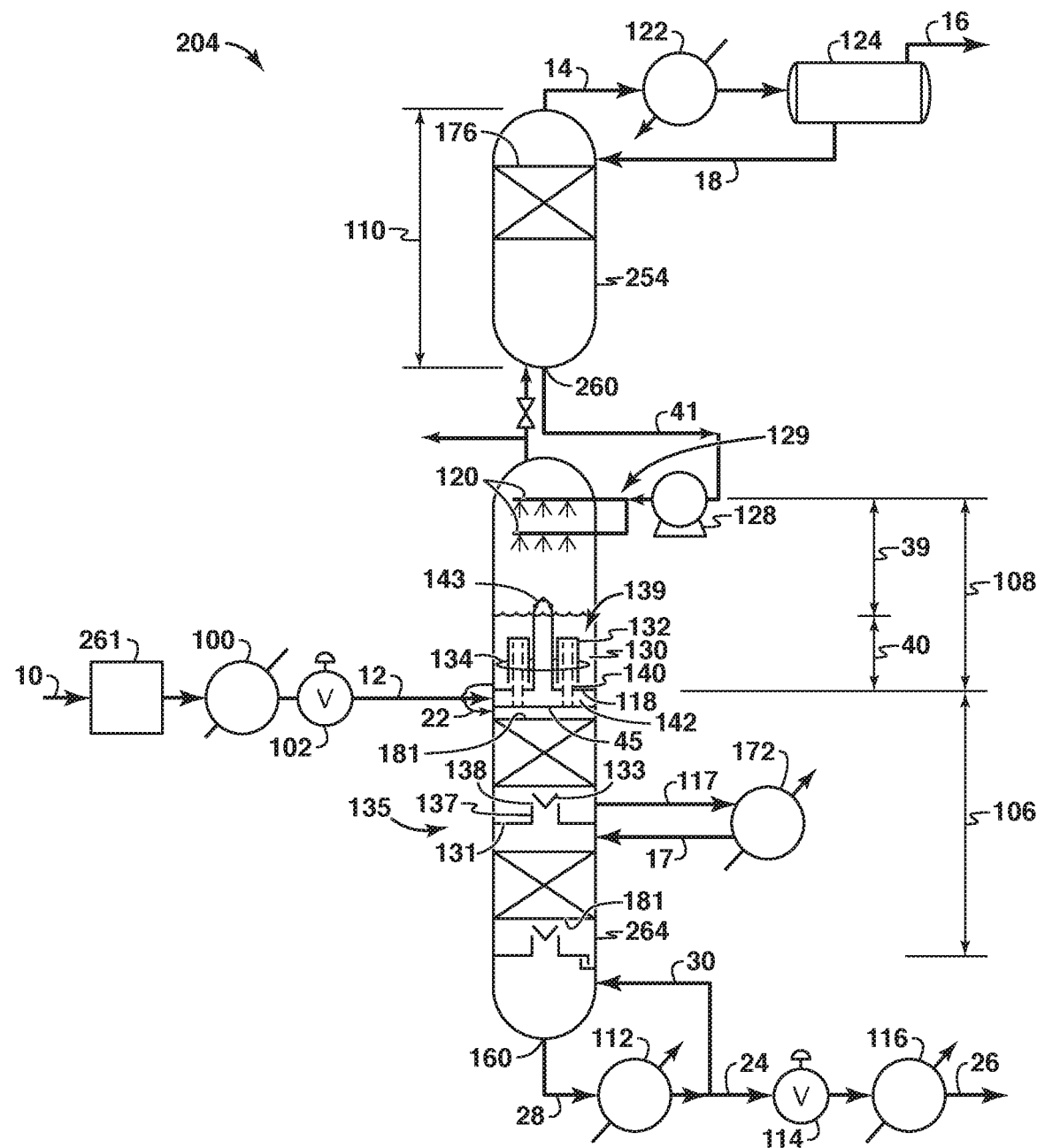
FIG. 2 is a schematic diagram of a tower with sections within multiple vessels according to disclosed aspects.

The system and method may separate a feed stream having methane and contaminants. The system may comprise a distillation tower 104, 204 (FIGS. 1-2). The distillation tower 104, 204 may separate the contaminants from the methane.

The distillation tower 104, 204 may be separated into three functional sections: a lower section 106, a middle controlled freeze zone section 108 and an upper section 110. The distillation tower 104, 204 may incorporate three functional sections when the upper section 110 is needed and/or desired.

The distillation tower 104, 204 may incorporate only two functional sections when the upper section 110 is not needed and/or desired. When the distillation tower does not include an upper section 110, a portion of vapor leaving the middle controlled freeze zone section 108 may be condensed in a condenser 122 and returned as a liquid stream via a spray assembly 129. Moreover, lines 18 and 20 may be eliminated, elements 124 and 126 may be one and the same, and elements 150 and 128 may be one and the same. The stream in line 14, now taking the vapors leaving the middle controlled freeze section 108, directs these vapors to the condenser 122.

The lower section 106 may also be referred to as a stripper section. The middle controlled freeze zone section 108 may also be referred to as a controlled freeze zone section. The upper section 110 may also be referred to as a rectifier section.

Figure 3:
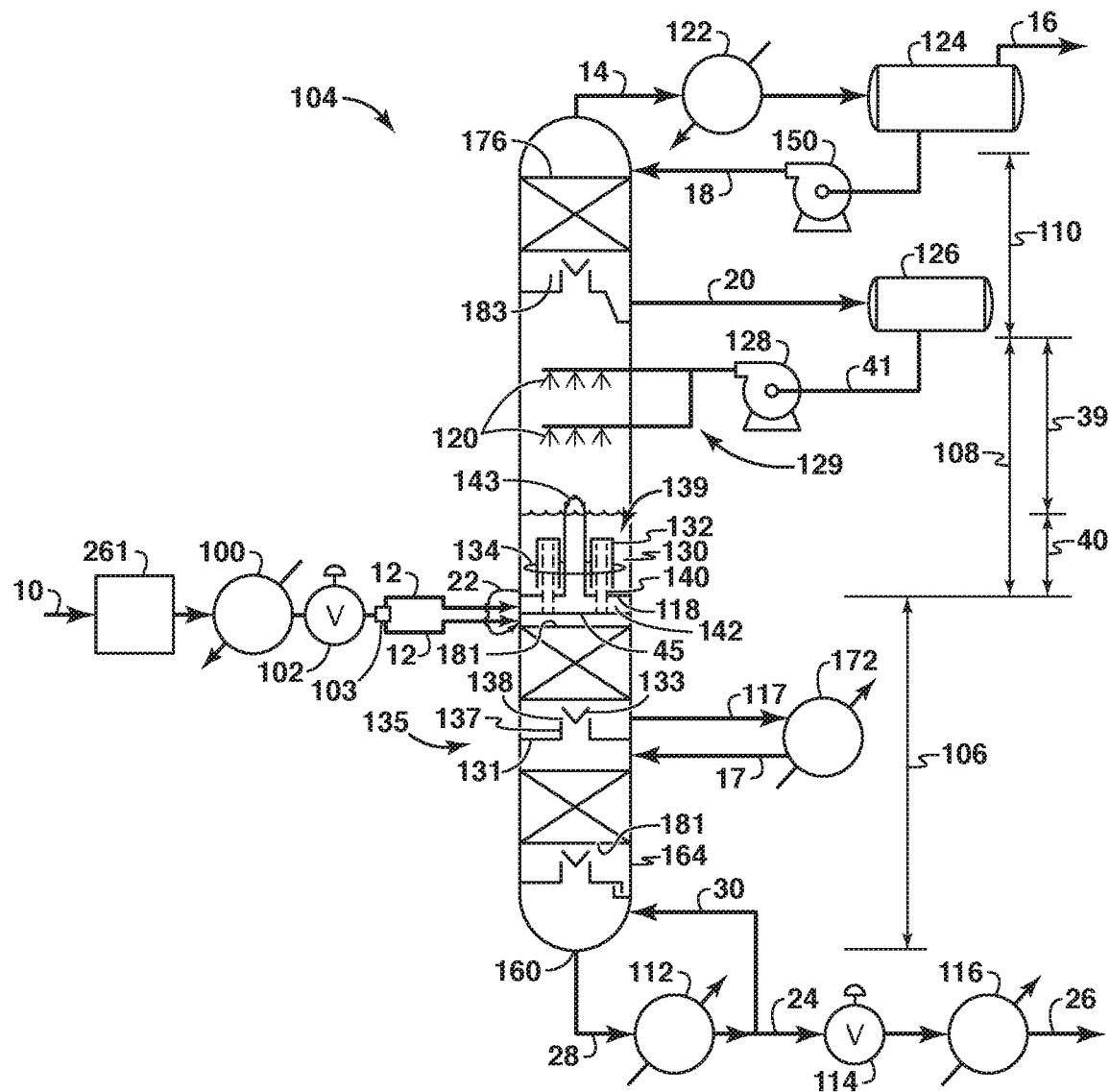
FIG. 3 is a schematic diagram of a tower with sections within a single vessel according to disclosed aspects.

The sections of the distillation tower 104 may be housed within a single vessel (FIGS. 1 and 3). For example, the lower section 106, the middle controlled freeze zone section 108, and the upper section 110 may be housed within a single vessel 164.

Figure 4:
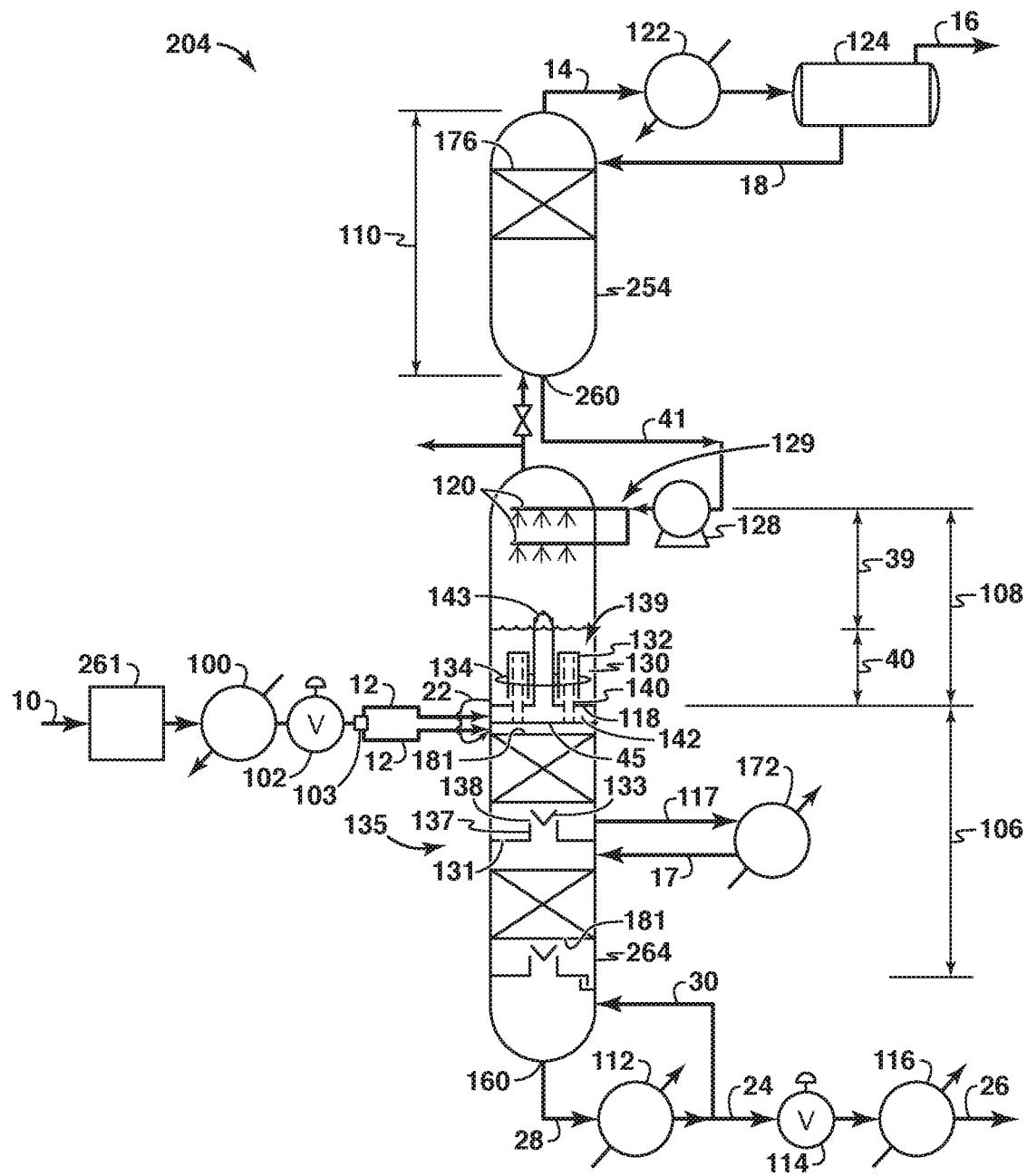
FIG. 4 is a schematic diagram of a tower with sections within multiple vessels according to disclosed aspects.

The sections of the distillation tower 204 may be housed within a plurality of vessels to form a split-tower configuration (FIGS. 2 and 4). Each of the vessels may be separate from the other vessels. Piping and/or another suitable mechanism may connect one vessel to another vessel. In this instance, the lower section 106, middle controlled freeze zone section 108 and upper section 110 may be housed within two or more vessels. For example, as shown in FIGS. 2 and 4, the upper section 110 may be housed within a single vessel 254 and the lower and middle controlled freeze zone sections 106, 108 may be housed within a single vessel 264. When this is the case, a liquid stream exiting the upper section 110, may exit through a liquid outlet bottom 260. The liquid outlet bottom 260 is at the bottom of the upper section 110. Although not shown, each of the sections may be housed within its own separate vessel, or one or more section may be housed within separate vessels, or the upper and middle controlled freeze zone sections may be housed within a single vessel and the lower section may be housed within a single vessel, etc. When sections of the distillation tower are housed within vessels, the vessels may be side-by-side along a horizontal line and/or above each other along a vertical line.

The split-tower configuration may be beneficial in situations where the height of the distillation tower, motion considerations, and/or transportation issues, such as for remote locations, need to be considered. This split-tower configuration allows for the independent operation of one or more sections. For example, when the upper section is housed within a single vessel and the lower and middle controlled freeze zone sections are housed within a single vessel, independent generation of reflux liquids using a substantially contaminant-free, largely hydrocarbon stream from a packed gas pipeline or an adjacent hydrocarbon line, may occur in the upper section. And the reflux may be used to cool the upper section, establish an appropriate temperature profile in the upper section, and/or build up liquid inventory at the bottom of the upper section to serve as an initial source of spray liquids for the middle controlled freeze zone section. Moreover, the middle controlled freeze zone and lower sections may be independently prepared by chilling the feed stream, feeding it to the optimal location be that in the lower section or in the middle controlled freeze zone section, generating liquids for the lower and the middle controlled freeze zone sections, and disposing the vapors off the middle controlled freeze zone section while they are off specification with too high a contaminant content. Also, liquid from the upper section may be intermittently or continuously sprayed, building up liquid level in the bottom of the middle controlled freeze zone section and bringing the contaminant content in the middle controlled freeze zone section down and near steady state level so that the two vessels may be connected to send the vapor stream from the middle controlled freeze zone section to the upper section, continuously spraying liquid from the bottom of the upper section into the middle controlled freeze zone section and stabilizing operations into steady state conditions. The split tower configuration may utilize a sump of the upper section as a liquid receiver for the pump 128, therefore obviating the need for a liquid receiver 126 in FIGS. 1 and 3.

The system may also include a heat exchanger 100 (FIGS. 1-4). The feed stream 10 may enter the heat exchanger 100 before entering the distillation tower 104, 204. The feed stream 10 may be cooled within the heat exchanger 100. The heat exchanger 100 helps drop the temperature of the feed stream 10 to a level suitable for introduction into the distillation tower 104, 204.

The system may include an expander device 102 (FIGS. 1-4). The feed stream 10 may enter the expander device 102 before entering the distillation tower 104, 204. The feed stream 10 may be expanded in the expander device 102 after exiting the heat exchanger 100. The expander device 102 helps drop the temperature of the feed stream 10 to a level suitable for introduction into the distillation tower 104, 204. The expander device 102 may be any suitable device, such as a valve. If the expander device 102 is a valve, the valve may be any suitable valve that may aid in cooling the feed stream 10 before it enters the distillation tower 104, 204. For example, the valve 102 may comprise a Joule-Thompson (J-T) valve.

The system may include a feed separator 103 (FIGS. 3-4). The feed stream may enter the feed separator before entering the distillation tower 104, 204. The feed separator may separate a feed stream having a mixed liquid and vapor stream into a liquid stream and a vapor stream. Lines 12 may extend from the feed separator to the distillation tower 104, 204. One of the lines 12 may receive the vapor stream from the feed separator. Another one of the lines 12 may receive the liquid stream from the feed separator. Each of the lines 12 may extend to the same and/or different sections (i.e. middle controlled freeze zone, and lower sections) of the distillation tower 104, 204. The expander device 102 may or may not be downstream of the feed separator 103. The expander device 102 may comprise a plurality of expander devices 102 such that each line 12 has an expander device 102.

The system may include a dehydration unit 261 (FIGS. 1-4). The feed stream 10 may enter the dehydration unit 261 before entering the distillation tower 104, 204. The feed stream 10 enters the dehydration unit 261 before entering the heat exchanger 100 and/or the expander device 102. The dehydration unit 261 removes water from the feed stream 10 to prevent water from later presenting a problem in the heat exchanger 100, expander device 102, feed separator 103, or distillation tower 104, 204. The water can present a problem by forming a separate water phase (i.e., ice and/or hydrate) that plugs lines, equipment or negatively affects the distillation process. The dehydration unit 261 dehydrates the feed stream to a dew point sufficiently low to ensure a separate water phase does not form at any point downstream during the rest of the process. The dehydration unit may be any suitable dehydration mechanism, such as a molecular sieve or a glycol dehydration unit.

The system may include a filtering unit (not shown). The feed stream 10 may enter the filtering unit before entering the distillation tower 104, 204. The filtering unit may remove undesirable contaminants from the feed stream before the feed stream enters the distillation tower 104, 204. Depending on what contaminants are to be removed, the filtering unit may be before or after the dehydration unit 261 and/or before or after the heat exchanger 100.

The system may include lines 12. Each of the lines may be referred to as an inlet channel 12. The feed stream is introduced into the distillation tower 104, 204 through one of the lines 12. One or more lines 12 may extend to the lower section 106 or the middle controlled freeze zone section 108 of the distillation tower 104, 204 to another of the lines 12. For example, the line 12 may extend to the lower section 106 such that the feed stream 10 may enter the lower section 106 of the distillation tower 104, 204 (FIGS. 1-4). Each line 12 may directly or indirectly extend to the lower section 106 or the middle controlled freeze zone section 108. Each line 12 may extend to an outer surface of the distillation tower 104, 204 before entering the distillation tower.

If the system includes the feed separator 103 (FIGS. 3-4), the line 12 may comprise a plurality of lines 12. Each line may be the same line as one of the lines that extends from the feed separator to a specific portion of the distillation tower 104, 204.

Before entering the distillation tower 104, 204, a sample of the feed stream 10 may enter an analyzer (not shown). The sample of the feed stream 10 may be a small sample of the feed stream 10. The feed stream 10 may comprise feed from multiple feed sources or feed from a single feed source. Each feed source may comprise, for example, a separate reservoir, one or more wellbores within one or more reservoirs, etc. The analyzer may determine the percentage of $CO_2$ in the sample of the feed stream 10 and, therefore, the content of $CO_2$ in the feed stream 10. The analyzer may connect to multiple lines 12 so that the feed stream 10 can be sent to one or more sections 106, 108 of the distillation tower 104, 204 after the sample of the feed stream 10 exits the analyzer. If the analyze determines that the percentage of $CO_2$ is greater than about 20% or greater than 20%, the analyzer may direct the feed stream to the line 12 extending from the lower section 106. If the analyzer determines that the percentage of $CO_2$ is less than about 20% or less than 20%, the analyzer may direct the feed stream to the line 12 extending from the middle controlled freeze zone section 108. The analyzer may be any suitable analyzer. For example, the analyzer may be a gas chromatograph or an IR analyzer. The analyzer may be positioned before the feed stream 10 enters the heat exchanger 100. The feed stream 10 entering the analyzer may be a single phase.

While the feed stream 10 may be introduced into any section of the distillation tower 104, 204 regardless of the percentage of $CO_2$ in the feed stream 10, it is more efficient to introduce the feed stream 10 into the section of the distillation tower 104, 204 that will employ the best use of energy. For this reason, it is preferable to introduce the feed stream to the lower section 106 when the percentage of $CO_2$ in the feed stream is greater than any percentage about 20% or greater than 20% and to the middle controlled freeze zone section 108 when the percentage of $CO_2$ in the feed stream is any percentage less than about 20% or less than 20%.

The feed stream may be directly or indirectly fed to one of the sections 106, 108. Thus, for the best use of energy it is best to introduce the feed stream into the distillation tower 104, 204 at the point in the distillation process of the distillation tower 104, 204 that matches the relevant percentage or content of $CO_2$ in the feed stream.

The feed stream 10 may enter a feed separator 103. The feed separator 103 separates a feed stream vapor portion from a feed stream liquid portion before the feed stream is introduced into the distillation tower 104, 204. The feed stream vapor portion may be fed to a different section or portion within a section of the distillation tower 104, 204 than the feed stream liquid portion. For example, the feed stream vapor portion may be fed to an upper controlled freeze zone section 39 of the middle controlled freeze zone section 108 and/or the feed stream liquid portion may be fed to a lower controlled freeze zone section 40 of the middle controlled freeze zone section 108 or to the lower section 106 of the distillation tower.

The lower section 106 is constructed and arranged to separate the feed stream 10 into an enriched contaminant bottom liquid stream (i.e., liquid stream) and a freezing zone vapor stream (i.e., vapor stream). The lower section 106 separates the feed stream at a temperature and pressure at which no solids form. The liquid stream may comprise a greater quantity of contaminants than of methane. The vapor stream may comprise a greater quantity of methane than of contaminants. In any case, the vapor stream is lighter than the liquid stream. As a result, the vapor stream rises from the lower section 106 and the liquid stream falls to the bottom of the lower section 106.

The lower section 106 may include and/or connect to equipment that separates the feed stream. The equipment may comprise any suitable equipment for separating methane from contaminants, such as one or more packed sections 181, or one or more distillation trays with perforations downcomers and weirs (FIGS. 1-4).

The equipment may include components that apply heat to the stream to form the vapor stream and the liquid stream. For example, the equipment may comprise a first reboiler 112 that applies heat to the stream. The first reboiler 112 may be located outside of the distillation tower 104, 204. The equipment may also comprise a second reboiler 172 that applies heat to the stream. The second reboiler 172 may be located outside of the distillation tower 104, 204. Line 117 may lead from the distillation tower to the second reboiler 172. Line 17 may lead from the second reboiler 172 to the distillation tower. Additional reboilers, set up similarly to the second reboiler described above, may also be used.

The first reboiler 112 may apply heat to the liquid stream that exits the lower section 106 through a liquid outlet 160 of the lower section 106. The liquid stream may travel from the liquid outlet 160 through line 28 to reach the first reboiler 112 (FIGS. 1-4). The amount of heat applied to the liquid stream by the first reboiler 112 can be increased to separate more methane from contaminants. The more heat applied by the reboiler 112 to the stream, the more methane separated from the liquid contaminants, though more contaminants will also be vaporized.

The first reboiler 112 may apply heat to the stream within the distillation tower 104, 204. Specifically, the heat applied by the first reboiler 112 warms up the lower section 106. This heat travels up the lower section 106 and supplies heat to warm solids entering a melt tray assembly 139 (FIGS. 1-4) of the middle controlled freeze zone section 108 so that the solids form a liquid and/or slurry mix.

The second reboiler 172 applies heat to the stream within the lower section 106. This heat is applied closer to the middle controlled freeze zone section 108 than the heat applied by the first reboiler 112. As a result, the heat applied by the second reboiler 172 reaches the middle controlled freeze zone section 108 faster than the heat applied by the first reboiler 112. The second reboiler 172 also helps with energy integration.

The equipment may include one or more chimney assemblies 135 (FIGS. 1-4). While falling to the bottom of the lower section 106, the liquid stream may encounter one or more of the chimney assemblies 135.

Each chimney assembly 135 includes a chimney tray 131 that collects the liquid stream within the lower section 106. The liquid stream that collects on the chimney tray 131 may be fed to the second reboiler 172. After the liquid stream is heated in the second reboiler 172, the stream may return to the middle controlled freeze zone section 108 to supply heat to the middle controlled freeze zone section 108 and/or the melt tray assembly 139. Unvaporized stream exiting the second reboiler 172 may be fed back to the distillation tower 104, 204 below the chimney tray 131. Vapor stream exiting the second reboiler 172 may be routed under or above the chimney tray 131 when the vapor stream enters the distillation tower 104, 204.

The chimney tray 131 may include one or more chimneys 137. The chimney 137 serves as a channel that the vapor stream in the lower section 106 traverses. The vapor stream travels through an opening in the chimney tray 131 at the bottom of the chimney 137 to the top of the chimney 137. The opening is closer to the bottom of the lower section 106 than it is to the bottom of the middle controlled freeze zone section 108. The top is closer to the bottom of the middle controlled freeze zone section 108 than it is to the bottom of the lower section 106.

Each chimney 137 has attached to it a chimney cap 133. The chimney cap 133 covers a chimney top opening 138 of the chimney 137. The chimney cap 133 prevents the liquid stream from entering the chimney 137. The vapor stream exits the chimney assembly 135 via the chimney top opening 138.

After falling to the bottom of the lower section 106, the liquid stream exits the distillation tower 104, 204 through the liquid outlet 160. The liquid outlet 160 is within the lower section 106 (FIGS. 1-4). The liquid outlet 160 may be located at the bottom of the lower section 106.

After exiting through the liquid outlet 160, the feed stream may travel via line 28 to the first reboiler 112. The feed stream may be heated by the first reboiler 112 and vapor may then re-enter the lower section 106 through line 30. Unvaporized liquid may continue out of the distillation process via line 24.

The systems may include an expander device 114 (FIGS. 1-4). After entering line 24, the heated liquid stream may be expanded in the expander device 114. The expander device 114 may be any suitable device, such as a valve. The valve 114 may be any suitable valve, such as a J-T valve.

The system may include a heat exchanger 116 (FIGS. 1-4). The liquid stream heated by the first reboiler 112 may be cooled or heated by the heat exchanger 116. The heat exchanger 116 may be a direct heat exchanger or an indirect heat exchanger. The heat exchanger 116 may comprise any suitable heat exchanger. After exiting the heat exchanger 116, the liquid stream exits the distillation process via line 26.

The vapor stream in the lower section 106 rises from the lower section 106 to the middle controlled freeze zone section 108. The middle controlled freeze zone section 108 is constructed and arranged to separate the feed stream 10 introduced into the middle controlled freeze zone section, or into the top of lower section 106, into a solid and a vapor stream. The middle controlled freeze zone section 108 forms a solid, which may be comprised more of contaminants than of methane. The vapor stream (i.e., methane-enriched vapor stream) may comprise more methane than contaminants.

The middle controlled freeze zone section 108 includes a lower section 40 and an upper section 39. The lower section 40 is below the upper section 39. The lower section 40 directly abuts the upper section 39. The lower section 40 is primarily but not exclusively a heating section of the middle controlled freeze zone section 108. The upper section 39 is primarily but not exclusively a cooling section of the middle controlled freeze zone section 108. The temperature and pressure of the upper section 39 are chosen so that the solid can form in the middle controlled freeze zone section 108.

The middle controlled freeze zone section 108 may comprise a melt tray assembly 139 that is maintained in the middle controlled freeze zone section 108 (FIGS. 1-4). The melt tray assembly 139 is within the lower section 40 of the middle controlled freeze zone section 108. The melt tray assembly 139 is not within the upper section 39 of the middle controlled freeze zone section 108.

The melt tray assembly 139 is constructed and arranged to melt solids formed in the middle controlled freeze zone section 108. When the warm vapor stream rises from the lower section 106 to the middle controlled freeze zone section 108, the vapor stream immediately encounters the melt tray assembly 139 and supplies heat to melt the solids. As shown in FIGS. 1-4 and more particularly in FIGS. 5-7, the melt tray assembly 139 may comprise at least one of a melt tray 118, a bubble cap 132, a vapor stream riser 140, a feed stream manifold 142, a feed stream riser 143, a liquid 130 and heat mechanism(s) 134.

The melt tray 118 may collect a liquid and/or slurry mix. The melt tray 118 divides at least a portion of the middle controlled freeze zone section 108 from the lower section 106. The melt tray 118 is at the bottom 45 of the middle controlled freeze zone section 108.

One or more vapor stream risers 140 have an inlet on the lower side of the melt tray 118 and is open to the lower section 106. FIG. 6, which is a bottom view of the feed stream manifold 142, shows the open lower ends of the vapor stream risers 140. The vapor stream risers 140 may act as a channel for the vapor stream rising from the lower section 106 to the middle controlled freeze zone section 108. The bubble cap 132 may provide a path for the vapor stream up the vapor stream riser 140 and then down and around the vapor stream riser 140 into the liquid 130 above the melt tray 118. The bubble cap 132 prevents the liquid 130 from travelling into the vapor stream riser 140 and also helps prevent solids from travelling into the vapor stream riser 140. The vapor stream's traversal through the bubble cap 132 allows the vapor stream to transfer heat to the liquid 130 within the melt tray assembly 139.

As shown more clearly in FIG. 5, lines 12 feed the feed stream into the feed stream manifold 142. The feed stream manifold distributes the feed stream to one or more feed stream risers 143. Feed stream risers 143 are designed to pass the feed stream through the melt tray 118 before being released into the open space above the liquid 130 without contacting the liquid 130. The feed stream manifold 142 may be constructed as part of the melt tray 118 or by using separate piping components. The feed stream manifold may be placed on the top side or the bottom side of the melt tray 118, and in a preferred aspect the feed stream manifold is placed on the bottom side of the tray as depicted in FIG. 5.

The upper end of the feed stream risers 143 may be open or, as shown in FIG. 5, may include a distribution cap 144 to further aid in providing an even introduction of the feed stream into the distillation tower 104, 204. The distribution cap may include openings 145 designed for optimal feed stream distribution. To further improve diffusion or distribution of the feed stream, the distribution cap may also have a cap or tray 146 positioned above the distribution cap. The cap or tray 146 may be angled as shown in FIG. 5 to limit solid carbon dioxide accumulation thereon. The cap or tray may be solid or may be perforated to create the desired diffusion of the feed stream. Other steps can be taken to further prevent solids accumulation, such as increasing the temperature of the feed stream passing through the feed stream risers. Another anti-solids strategy would be to install internal fins (not shown) on the inner portion of the feed stream risers 143 to increase the temperature of the feed stream risers 143. Still another anti-solids strategy is to treat the surface of the portion of the riser that extends above the level of the liquid 130. Such surface treatments may include the addition of a non-stick coating, such as polyfluorotetraethylene (PFTE), or alternatively may include a surface finish, such as electropolishing, to the portion of the feed stream risers 143 extending above the level of liquid 130. These and other surface treatments are more fully described in United States Patent Application Publication No. 2015/0159942, titled "Method and Device for Separating Hydrocarbons and Contaminants with a Surface Treatment Mechanism" and commonly owned herewith, the disclosure of which is incorporated herein by reference in its entirety.

The number and size of vapor risers 140, bubble caps 132, and feed stream risers 143 should be selected based on the expected flow rates of the feed stream for a specific application. Additionally, the vapor risers 140 and the feed stream risers 143 should be evenly distributed across the cross-section of the distillation tower 104, 204. FIGS. 5-7 depict one example of riser placement, and other riser placement strategies are considered to be within the scope of the disclosure.

One or more heat mechanisms 134 may further heat up the liquid 130 to facilitate melting of the solids into a liquid and/or slurry mix. The heat mechanism(s) 134 may be located anywhere within the melt tray assembly 139. For example, as shown in FIGS. 1-4, a heat mechanism 134 may be located around bubble caps 132. The heat mechanism 134 may be any suitable mechanism, such as a heat coil. The heat source of the heat mechanism 134 may be any suitable heat source.

The liquid 130 in the melt tray assembly is heated by the vapor stream. The liquid 130 may also be heated by the one or more heat mechanisms 134. The liquid 130 helps melt the solids formed in the middle controlled freeze zone section 108 into a liquid and/or slurry mix. Specifically, the heat transferred by the vapor stream heats up the liquid, thereby enabling the heat to melt the solids. The temperature of liquid 130 may be at a level sufficient to melt the solids. Other methods may be used to increase the temperature of the liquid, for example, the apparatus and method described in U.S. Provisional Patent Application titled "Alternate Mixing and Heat Integration of a Melt Tray in a Cryogenic Distillation Tower," being commonly owned and filed on an even date herewith, the disclosure of which is incorporated herein by reference in its entirety.

The middle controlled freeze zone section 108 may also comprise a spray assembly 129. The spray assembly 129 cools the vapor stream that rises from the lower section 40. The spray assembly 129 sprays liquid, which is cooler than the vapor stream, on the vapor stream to cool the vapor stream. The spray assembly 129 is within the upper section 39. The spray assembly 129 is not within the lower section 40. The spray assembly 129 is above the melt tray assembly 139. In other words, the melt tray assembly 139 is below the spray assembly 129.

The spray assembly 129 includes one or more spray nozzles 120 (FIGS. 1-4). Each spray nozzle 120 sprays liquid on the vapor stream. The spray assembly 129 may also include a spray pump 128 (FIGS. 1-4) that pumps the liquid. Instead of a spray pump 128, gravity may induce flow in the liquid.

The liquid sprayed by the spray assembly 129 contacts the vapor stream at a temperature and pressure at which solids form. Solids, containing mainly contaminants, form when the sprayed liquid contacts the vapor stream. The solids fall toward the melt tray assembly 139.

The temperature in the middle controlled freeze zone section 108 cools down as the vapor stream travels from the bottom of the middle controlled freeze zone section 108 to the top of the middle controlled freeze zone section 108. The methane in the vapor stream rises from the middle controlled freeze zone section 108 to the upper section 110. Some contaminants may remain in the methane and also rise. The contaminants in the vapor stream tend to condense or solidify with the colder temperatures and fall to the bottom of the middle controlled freeze zone section 108.

The solids form the liquid and/or slurry mix when in the liquid 130. The liquid and/or slurry mix flows from the middle controlled freeze zone section 108 to the lower distillation section 106. The liquid and/or slurry mix flows from the bottom of the middle controlled freeze zone section 108 to the top of the lower section 106 via a line 22 (FIGS. 1-4). The line 22 may be an exterior line. The line 22 may extend from the distillation tower 104, 204. The line 22 may extend from the middle controlled freeze zone section 108. The line may extend to the lower section 106. The line 22 may extend from an outer surface of the distillation tower 104, 204.

As shown in FIGS. 1-2, the vapor stream that rises in the middle controlled freeze zone section 108 and does not form solids or otherwise fall to the bottom of the middle controlled freeze zone section 108, rises to the upper section 110. The upper section 110 operates at a temperature and pressure and contaminant concentration at which no solid forms. The upper section 110 is constructed and arranged to cool the vapor stream to separate the methane from the contaminants. Reflux in the upper section 110 cools the vapor stream. The reflux is introduced into the upper section 110 via line 18. Line 18 may extend to the upper section 110. Line 18 may extend from an outer surface of the distillation tower 104, 204.

After contacting the reflux in the upper section 110, the feed stream forms a vapor stream and a liquid stream. The vapor stream mainly comprises methane. The liquid stream comprises relatively more contaminants. The vapor stream rises in the upper section 110 and the liquid falls to a bottom of the upper section 110.

To facilitate separation of the methane from the contaminants when the stream contacts the reflux, the upper section 110 may include one or more mass transfer devices 176. Each mass transfer device 176 helps separate the methane from the contaminants. Each mass transfer device 176 may comprise any suitable separation device, such as a tray with perforations, or a section of random or structured packing to facilitate contact of the vapor and liquid phases.

After rising, the vapor stream may exit the distillation tower 104, 204 through line 14. The line 14 may emanate from an upper part of the upper section 110. The line 14 may extend from an outer surface of the upper section 110.

From line 14, the vapor stream may enter a condenser 122. The condenser 122 cools the vapor stream to form a cooled stream. The condenser 122 at least partially condenses the stream.

After exiting the condenser 122, the cooled stream may enter a separator 124. The separator 124 separates the vapor stream into liquid and vapor streams. The separator may be any suitable separator that can separate a stream into liquid and vapor streams, such as a reflux drum.

Once separated, the vapor stream may exit the separator 124 as sales product. The sales product may travel through line 16 for subsequent sale to a pipeline and/or condensation to be liquefied natural gas.

Once separated, the liquid stream may return to the upper section 110 through line 18 as the reflux. The reflux may travel to the upper section 110 via any suitable mechanism, such as a reflux pump 150 (FIGS. 1 and 3) or gravity (FIGS. 2 and 4).

The liquid stream (i.e., freezing zone liquid stream) that falls to the bottom of the upper section 110 collects at the bottom of the upper section 110. The liquid may collect on tray 183 (FIGS. 1 and 3) or at the bottommost portion of the upper section 110 (FIGS. 2 and 4). The collected liquid may exit the distillation tower 104, 204 through line 20 (FIGS. 1 and 3) or outlet 260 (FIGS. 2 and 4). The line 20 may emanate from the upper section 110. The line 20 may emanate from a bottom end of the upper section 110. The line 20 may extend from an outer surface of the upper section 110.

The line 20 and/or outlet 260 connect to a line 41. The line 41 leads to the spray assembly 129 in the middle controlled freeze zone section 108. The line 41 emanates from the holding vessel 126. The line 41 may extend to an outer surface of the middle controlled freeze zone section 108.

The line 20 and/or outlet 260 may directly or indirectly (FIGS. 1-4) connect to the line 41. When the line 20 and/or outlet 260 directly connect to the line 41, the liquid spray may be pumped to the spray nozzle(s) 120 via any suitable mechanism, such as the spray pump 128 or gravity. When the line 20 and/or outlet 260 indirectly connect to the line 41, the lines 20, 41 and/or outlet 260 and line 41 may directly connect to a holding vessel 126 (FIGS. 1 and 3). The holding vessel 126 may house at least some of the liquid spray before it is sprayed by the nozzle(s). The liquid spray may be pumped from the holding vessel 126 to the spray nozzle(s) 120 via any suitable mechanism, such as the spray pump 128 (FIGS. 1-2) or gravity. The holding vessel 126 may be needed when there is not a sufficient amount of liquid stream at the bottom of the upper section 110 to feed the spray nozzles 120.

Figure 8:
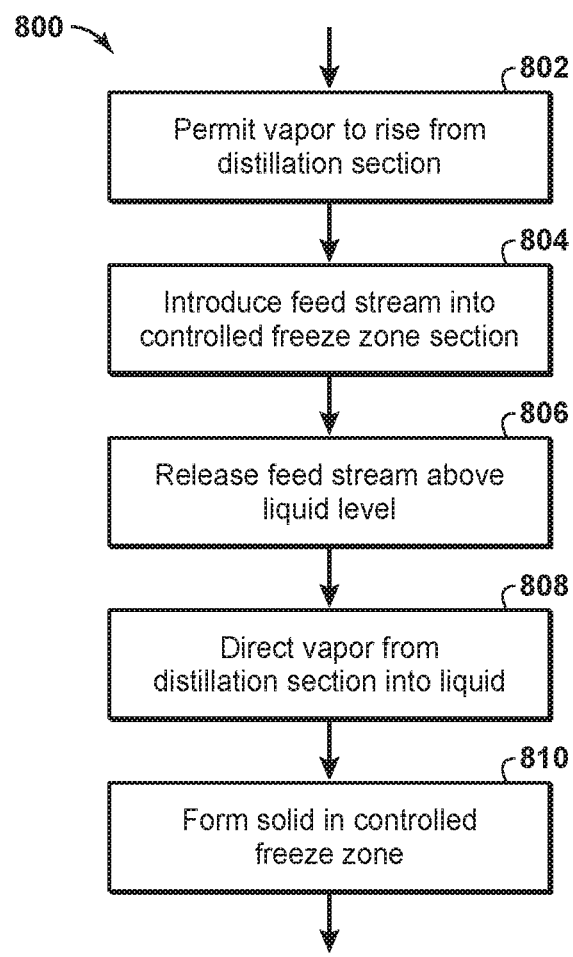
FIG. 8 is a flowchart of a method within the scope of the present disclosure.

FIG. 8 is a flowchart showing a method 800 of separating a feed stream in a distillation tower according to aspects of the disclosure. At block 802 vapor is permitted to rise upwardly from a distillation section of the distillation tower. At block 804 a feed stream is introduced into a controlled freeze zone section of the distillation tower. The controlled freeze zone section is situated above the distillation section. At block 806 the feed stream is released above a level of a liquid retained by a melt tray assembly in the controlled freeze zone section. At block 808 vapor from the distillation section is directed into the liquid retained by the melt tray assembly. At block 810 a solid is formed from the feed stream in the controlled freeze zone section.

The steps depicted in FIG. 8 are provided for illustrative purposes only and a particular step may not be required to perform the inventive methodology. The claims, and only the claims, define the inventive system and methodology.

Disclosed aspects may be used in hydrocarbon management activities. As used herein, "hydrocarbon management" or "managing hydrocarbons" includes hydrocarbon extraction, hydrocarbon production, hydrocarbon exploration, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities. The term "hydrocarbon management" is also used for the injection or storage of hydrocarbons or $CO_2$, for example the sequestration of $CO_2$, such as reservoir evaluation, development planning, and reservoir management. The disclosed methodologies and techniques may be used to produce hydrocarbons in a feed stream extracted from, for example, a subsurface region. The feed stream extracted may be processed in the distillation tower 104, 204 and separated into hydrocarbons and contaminants. The separated hydrocarbons exit the middle controlled freeze zone section 108 or the upper section 110 of the distillation tower. Some or all of the hydrocarbons that exit are produced. Hydrocarbon extraction may be conducted to remove the feed stream from for example, the subsurface region, which may be accomplished by drilling a well using oil well drilling equipment. The equipment, and techniques used to drill a well and/or extract the hydrocarbons are well known by those skilled in the relevant art. Other hydrocarbon extraction activities and, more generally, other hydrocarbon management activities, may be performed according to known principles.

Aspects of the disclosure may include any combinations of the methods and systems shown in the following numbered paragraphs. This is not to be considered a complete listing of all possible aspects, as any number of variations can be envisioned from the description above.

1. A distillation tower for separating a feed stream, the distillation tower comprising:
   a distillation section permitting vapor to rise upwardly therefrom;
   a controlled freeze zone section situated above the distillation section, the controlled freeze zone constructed and arranged to form a solid from a feed stream, the controlled freeze zone section including
      a spray assembly in the controlled freeze zone upper section, and
      a melt tray assembly in the controlled freeze zone lower section;
      wherein the melt tray assembly includes
      a feed stream manifold that directs the feed stream into the distillation tower,
      at least one vapor stream riser that directs the vapor from the distillation section into liquid retained by the melt tray assembly, and
      at least one feed stream riser having a lower end operationally connected to the feed stream manifold and an upper end positioned above a level of the liquid retained by the melt tray assembly, wherein the feed stream is released above the level of the liquid retained by the melt tray assembly.

2. The distillation tower of paragraph 1, wherein the at least one vapor stream riser passes through the feed stream manifold without mixing the feed stream with the vapor stream from the distillation section.

3. The distillation tower of paragraph 1 or paragraph 2, further comprising:
   a distribution cap disposed on an upper end of one or more of the at least one feed stream risers, the distribution cap configured to distribute the feed stream throughout the controlled freeze zone section.

4. The distillation tower of paragraph 3, further comprising openings on the top of the distribution cap to permit the feed stream to pass therethrough.

5. The distillation tower of any one of paragraphs 1-4, further comprising a cap or tray positioned above the distribution cap, the cap or tray further distributing the feed stream throughout the controlled freeze zone section.

6. The distillation tower of any one of paragraphs 1-5, further comprising:
   a bubble cap arranged above each of the at least one vapor risers, each bubble cap arranged above an upper end of the respective vapor riser, the bubble cap having a closed upper end and an open lower end, the open lower end situated below the level of the liquid retained by the melt tray assembly.

7. The distillation tower of any one of paragraphs 1-6, wherein the controlled freeze zone further comprises:
   a spray assembly arranged above the melt tray assembly, the spray assembly configured to spray a liquid into the feed stream exiting the at least one feed stream riser.

8. The distillation tower of any one of paragraphs 1-7, wherein the melt tray assembly further comprises a heating mechanism configured to heat the liquid retained by the melt tray assembly.

9. The distillation tower of paragraph 1, wherein the feed stream comprises a hydrocarbon and a contaminant, and wherein the feed stream contains less than 30% contaminant when introduced into the controlled freeze zone section.

10. A method of separating a feed stream in a distillation tower, the method comprising:
    permitting vapor to rise upwardly from a distillation section of the distillation tower;
    introducing a feed stream into a controlled freeze zone section of the distillation tower, the controlled freeze zone section being situated above the distillation section;
    releasing the feed stream above a level of a liquid retained by a melt tray assembly in the controlled freeze zone section;
    directing vapor from the distillation section into the liquid retained by the melt tray assembly; and
    forming a solid from the feed stream in the controlled freeze zone section.

11. The method of paragraph 10, wherein the feed stream is introduced into the controlled freeze zone section using a feed stream manifold.

12. The method of paragraph 11, further comprising:
    directing the feed stream from the feed stream manifold and through at least one feed stream riser, each of the at least one feed stream risers positioned to pass through the liquid retained by the melt tray assembly and having an upper end situated above said liquid, thereby permitting the feed stream to be released above the level of the liquid.

13. The method of paragraph 12, further comprising:
    evenly distributing, throughout the controlled freeze zone section, the feed stream exiting the upper end of the at least one feed stream riser.

14. The method of paragraph 13, wherein evenly distributing the feed stream comprises directing the feed stream through openings on a distribution cap disposed on the upper end of each of the at least one feed stream risers.

15. The method of any one of paragraphs 10-14, wherein directing the vapor from the distillation section into the liquid is accomplished without mixing the vapor with the feed stream.

16. The method of any one of paragraphs 10-15, wherein directing the vapor from the distillation section in the liquid is accomplished using at least one vapor stream riser having a lower end positioned to accept vapor from the distillation section and an upper end below a level of the liquid retained by the melt tray assembly.

17. The method of paragraph 14, further comprising:
providing a bubble cap on the upper end of one or more of the at least one vapor stream riser, the bubble cap directing the vapor downwardly into the liquid retained by the melt tray assembly.

18. The method of any one of paragraphs 10-17, further comprising:
spraying a liquid into the feed stream after the feed stream has been released above the liquid retained by the melt tray assembly.

It should be understood that numerous changes, modifications, and alternatives to the preceding disclosure can be made without departing from the scope of the disclosure. The preceding description, therefore, is not meant to limit the scope of the disclosure. Rather, the scope of the disclosure is to be determined only by the appended claims and their equivalents. It is also contemplated that structures and features in the present examples can be altered, rearranged, substituted, deleted, duplicated, combined, or added to each other.

What is claimed is:

1. A distillation tower for separating a feed stream, the distillation tower comprising:
   a distillation section permitting vapor to rise upwardly from said distillation section;
   a controlled freeze zone section situated above the distillation section, the controlled freeze zone constructed and arranged to form a solid from a feed stream, the controlled freeze zone section including
      a spray assembly in the controlled freeze zone upper section, and
      a melt tray assembly in the controlled freeze zone lower section;
   wherein the melt tray assembly includes
      a feed stream manifold that directs the feed stream into the distillation tower,
      at least one vapor stream riser that directs the vapor from the distillation section into liquid retained by the melt tray assembly, wherein the at least one vapor stream riser passes through the feed stream manifold without mixing the feed stream with the vapor stream from the distillation section, and
      at least one feed stream riser, each feed stream riser having a lower end operationally connected to the feed stream manifold and an upper end positioned above a level of the liquid retained by the melt tray assembly, wherein the feed stream is released above the level of the liquid retained by the melt tray assembly.

2. The distillation tower of claim 1, further comprising:
a distribution cap disposed on the upper end of one or more of the at least one feed stream risers, the distribution cap configured to distribute the feed stream throughout the controlled freeze zone section.

3. The distillation tower of claim 2, further comprising openings on the top of the distribution cap to permit the feed stream to pass through.

4. The distillation tower of claim 1, further comprising a cap or tray positioned above the distribution cap, the cap or tray further distributing the feed stream throughout the controlled freeze zone section.

5. The distillation tower of claim 1, further comprising:
a bubble cap arranged above each of the at least one vapor risers, each bubble cap arranged above an upper end of the respective vapor riser, the bubble cap having a closed upper end and an open lower end, the open lower end situated below the level of the liquid retained by the melt tray assembly.

6. The distillation tower of claim 1, wherein the controlled freeze zone further comprises:
the spray assembly arranged above the melt tray assembly, the spray assembly configured to spray a liquid into the feed stream exiting the at least one feed stream riser.

7. The distillation tower of claim 1, wherein the melt tray assembly further comprises a heating mechanism configured to heat the liquid retained by the melt tray assembly.

8. The distillation tower of claim 1, wherein the feed stream comprises a hydrocarbon and a contaminant, and wherein the feed stream contains less than 30% contaminant when introduced into the controlled freeze zone section.

* * * * *